US009375366B1

(12) United States Patent
Morisi

(10) Patent No.: US 9,375,366 B1
(45) Date of Patent: Jun. 28, 2016

(54) FEMININE HYGIENE PRODUCT DISPOSAL POUCH

(71) Applicant: Susan Morisi, Suffern, NY (US)

(72) Inventor: Susan Morisi, Suffern, NY (US)

(*) Notice: Subject to any disclaimer, the term of this patent is extended or adjusted under 35 U.S.C. 154(b) by 0 days.

(21) Appl. No.: 14/841,890

(22) Filed: Sep. 1, 2015

Related U.S. Application Data

(60) Provisional application No. 62/050,312, filed on Sep. 15, 2014.

(51) Int. Cl.
*A61F 13/15* (2006.01)
*A61F 13/551* (2006.01)
*B65D 71/08* (2006.01)

(52) U.S. Cl.
CPC ......... *A61F 13/5519* (2013.01); *A61F 13/5518* (2013.01); *B65D 71/08* (2013.01); *A61F 2013/55195* (2013.01)

(58) Field of Classification Search
CPC .................. A61F 13/5518; A61F 13/5519
USPC ......... 206/581, 484, 440, 438, 494, 233, 812; 383/84, 120, 41; 221/102; 132/312
See application file for complete search history.

(56) References Cited

U.S. PATENT DOCUMENTS

| | | | | |
|---|---|---|---|---|
| 2,764,201 A * | 9/1956 | Whippo | ............... | A45C 11/008 150/111 |
| 3,307,687 A * | 3/1967 | Steinman | ............. | A47K 10/421 206/229 |
| 3,889,804 A * | 6/1975 | Ravich | ....................... | F24J 1/00 206/221 |
| 4,182,336 A * | 1/1980 | Black | ..................... | A61F 13/551 206/438 |
| 4,332,319 A * | 6/1982 | Hurwood | ........... | B65D 81/3261 132/286 |
| 4,702,378 A * | 10/1987 | Finkel | .................... | A45C 11/00 206/581 |
| 4,879,442 A * | 11/1989 | Giovine | ............. | B65D 83/0888 206/233 |
| 4,919,302 A * | 4/1990 | McPherson | ............ | A47K 10/28 221/102 |
| D345,210 S | 3/1994 | Thomas | | |
| 5,524,764 A * | 6/1996 | Kaufman | ............... | A45D 37/00 132/309 |
| 5,638,957 A * | 6/1997 | Brasier | ................. | A61F 13/551 206/581 |
| 5,725,310 A * | 3/1998 | Kruczko | .............. | B65D 5/6611 229/117.05 |
| 6,004,307 A * | 12/1999 | Colon | ..................... | A61F 13/84 206/581 |
| 6,059,100 A * | 5/2000 | Jones | .................. | A61F 13/5515 206/210 |
| 6,350,931 B1 * | 2/2002 | Martin | ............. | A61F 13/55175 206/225 |
| 6,994,696 B2 * | 2/2006 | Suga | ................. | A61F 13/55185 604/14 |
| 7,104,977 B2 | 9/2006 | Price et al. | | |
| 7,490,734 B2 * | 2/2009 | Carr | ..................... | A47K 10/421 221/102 |
| 7,491,062 B2 * | 2/2009 | Suh | ..................... | A61F 13/5511 434/236 |

(Continued)

FOREIGN PATENT DOCUMENTS

| | | |
|---|---|---|
| WO | WO0152784 | 7/2001 |
| WO | WO2008035241 | 3/2008 |
| WO | WO2008133039 | 11/2008 |

*Primary Examiner* — King M Chu
(74) *Attorney, Agent, or Firm* — Goldstein Law Offices, P.C.

(57) ABSTRACT

A feminine hygiene product disposal pouch having an inner compartment and at least one partitioning barrier, such as a partitioning wall, defining a pair of chambers. A first chamber is adapted for housing an unused feminine hygiene product, and a second chamber houses a disposal container for discarding a plurality of feminine hygiene products and materials, including the pouch itself. In an example embodiment, at least one chamber is expandable for hygienically disposing of the feminine hygiene materials therein. The chambers can share a common sealed edge, such as a heated seal, for enabling simultaneous access to each of the compartments. In another example embodiment, the pouch includes a partitioning seam for defining the chambers such that the outer wall can be operably removed from each chamber in succession for accessing the contents therein.

12 Claims, 8 Drawing Sheets

(56) References Cited

U.S. PATENT DOCUMENTS

| | | |
|---|---|---|
| 7,942,857 B2 | 5/2011 | Chicoine et al. |
| 8,286,793 B2 | 10/2012 | Kondo et al. |
| 8,388,592 B1 | 3/2013 | Gentile et al. |
| 2002/0175094 A1* | 11/2002 | Campbell .......... B65D 83/0888 206/233 |
| 2005/0138896 A1* | 6/2005 | Snell ................ A61F 13/15747 53/429 |
| 2005/0147328 A1* | 7/2005 | Cheaure ................ B65D 31/12 383/38 |
| 2005/0263556 A1* | 12/2005 | Labit ...................... A45C 11/00 224/610 |
| 2008/0077104 A1* | 3/2008 | Baer ..................... A61F 13/551 604/385.13 |
| 2009/0152161 A1* | 6/2009 | St. Cyr .................. A45C 11/00 206/581 |
| 2011/0270210 A1 | 11/2011 | Rainho das Neves |

\* cited by examiner

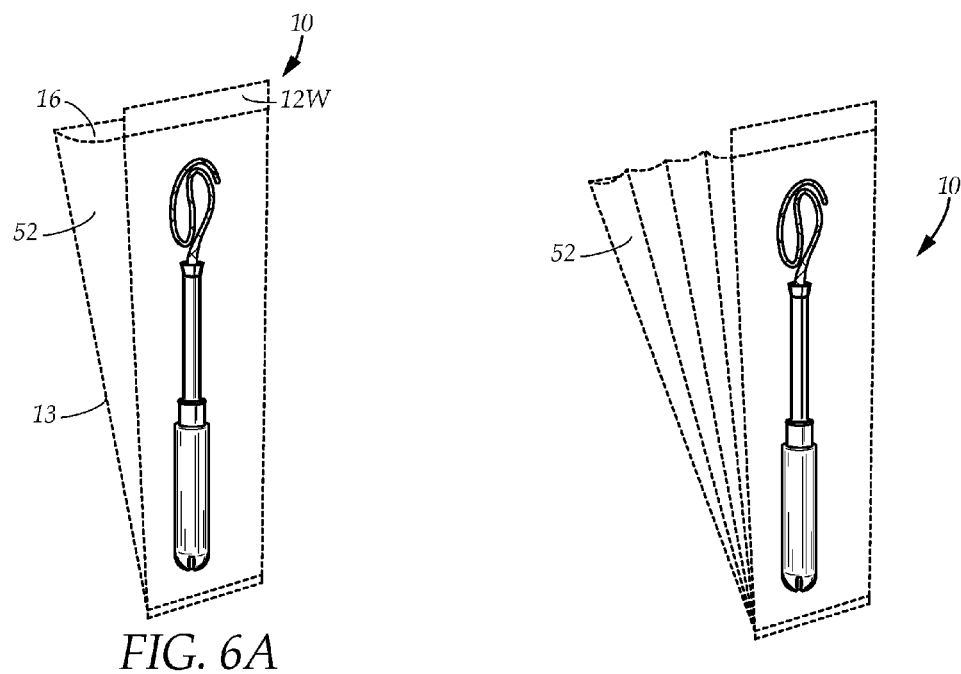
FIG. 6A
FIG. 6B
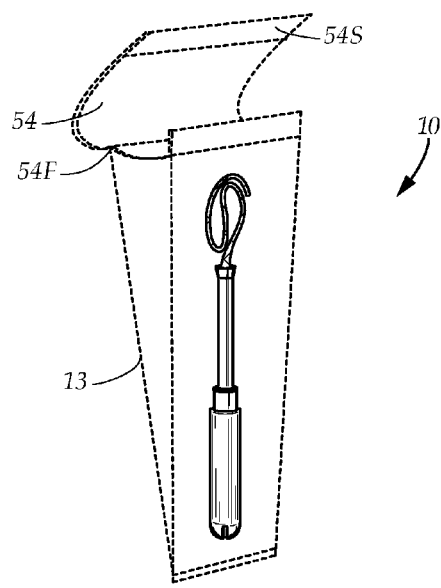
FIG. 6C

FEMININE HYGIENE PRODUCT DISPOSAL POUCH

CROSS-REFERENCE TO RELATED APPLICATIONS

This application is a nonprovisional utility application of provisional patent application, Ser. No. 62/050,312 filed in the United States Patent Office on Sep. 15, 2014 and claims the priority thereof and is expressly incorporated herein by reference in its entirety.

TECHNICAL FIELD

The present disclosure relates generally to a feminine hygiene product disposal pouch. More particularly, the present disclosure relates to a feminine hygiene product disposal pouch including at least a pair of chambers which cooperatively enable the hygienic and discreet disposal of feminine hygiene products.

BACKGROUND

Many women experience annoying and debilitating symptoms associated with menstruation. Amidst the cramps and the lack of energy lurks low self-confidence and anxiety which must be endured until the end of the monthly cycle when hormones once again normalize. Hormones, however, are not solely to blame for this lack of confidence and anxiety. The generally unaccommodating personal and public restrooms used by women to dispose of and change their feminine hygiene products, such as tampons, often exacerbate their anxiety.

Tampon use typically involves three components, an applicator, a tampon within the applicator, and the packaging in which the applicator is held. Many women try to reinsert the applicator in the packaging after its use, but find that the packaging has torn apart or is not big enough to be used for this purpose hygienically.

Most female bathrooms lack a trash receptacle within each stall within which to dispose of used tampons, tampon applicators, and tampon packaging. As a result, hygienic disposal of such feminine hygiene materials is a frustrating problem. Women sometimes try to flush all the tampon materials down the toilet. This practice often leads to clogged and overflowing toilets, and clogged sewage systems.

Further, the tampon components can be bulkily wrapped in large wads of toilet paper and disposed of in the trash receptacles. However, this method of disposal quickly overflows the receptacles, potentially violating medical waste disposal rules public establishments must follow. Consequently, many women find themselves having to endure the embarrassment of carrying their tampon and applicator out of the bathroom stall for disposal in a larger, public trash receptacle. However, this disposal is grossly unhygienic and humiliating as it rarely goes unwitnessed by another. In short, a discreet, compact, and sanitary manner for disposing of feminine hygiene products is needed.

While these units may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a complete and hygienic solution for feminine hygiene product disposal. Accordingly, the present disclosure provides an example embodiment of a feminine hygiene product disposal pouch which can be used for the disposal of a plurality of feminine hygiene materials, including at least a used tampon and a tampon applicator.

Another aspect of an example embodiment in the present disclosure is to provide a feminine hygiene product disposal pouch which is compact for discreetly disposing of feminine hygiene materials. Accordingly, the present disclosure provides an example embodiment of the feminine hygiene product disposal pouch having an outer wall which defines an inner compartment, and at least one partitioning barrier which divides the inner compartment into a pair of inner chambers, each chamber each suitably sized for the disposal of the feminine hygiene materials.

A further aspect of an example embodiment in the present disclosure is to provide a feminine hygiene product disposal pouch which is adjustable to accommodate a large number of feminine hygiene materials. Accordingly, the present disclosure provides an example embodiment of the feminine hygiene wrapper wherein one of the chambers includes a pair of side walls which are expandable for enabling the direct disposal of several feminine hygiene materials therein.

Yet a further aspect of an example embodiment in the present disclosure is to provide a feminine hygiene product disposal pouch which is easily opened for simultaneous access to each of the chambers therein. Accordingly, the present disclosure provides an example embodiment of the feminine hygiene product disposal pouch wherein the chambers include at least one common sealed edge shared by each of the chambers, such as a heated seal.

Still a further aspect of an example embodiment in the present disclosure is to provide a feminine hygiene product disposal pouch which can be discreetly and hygienically disposed of in a public area. Accordingly, the present disclosure provides an example embodiment of the feminine hygiene product disposal pouch including a disposal container within at least one of the chambers for discarding feminine hygiene materials including the feminine hygiene product disposal pouch itself.

Still a further aspect of an example embodiment in the present disclosure is to provide a feminine hygiene product disposal pouch which enables access to the disposal container and the unused tampon in succession. Accordingly, the present disclosure provides an example embodiment of the feminine hygiene wrapper wherein the partitioning barrier is a partitioning seam which defines the chambers such that the outer wall is removed from each chamber in succession for accessing the contents therein.

Accordingly, the present disclosure describes a feminine hygiene product disposal pouch having an inner compartment and at least one partitioning barrier, such as a partitioning wall, defining a pair of chambers. A first chamber is adapted for housing an unused feminine hygiene product, and a second chamber houses a disposal container for discarding a plurality of feminine hygiene products and materials, including the pouch itself. In an example embodiment, at least one chamber is expandable for hygienically disposing of the feminine hygiene materials therein. The chambers can share a common sealed edge, such as a heated seal, for enabling simultaneous access to each of the compartments. In another example embodiment, the pouch includes a partitioning seam for defining the chambers such that the outer wall can be operably removed from each chamber in succession for accessing the contents therein.

The present disclosure addresses at least one of the foregoing disadvantages. However, it is contemplated that the present disclosure may prove useful in addressing other problems and deficiencies in a number of technical areas. Therefore, the claims in this or any previous or subsequent application(s) should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

FIG. 6A is a perspective view of an example embodiment of the first example embodiment of the feminine hygiene product disposal pouch including at least one compartment having a pair of expandable side walls.

FIG. 6B, similar to 6A, is a perspective view of the first example embodiment wherein the side walls are accordion-folded.

FIG. 6C, similar to 6A, is a perspective view of the first example embodiment wherein at least one chamber has a flap for resealing the chamber.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 1A:
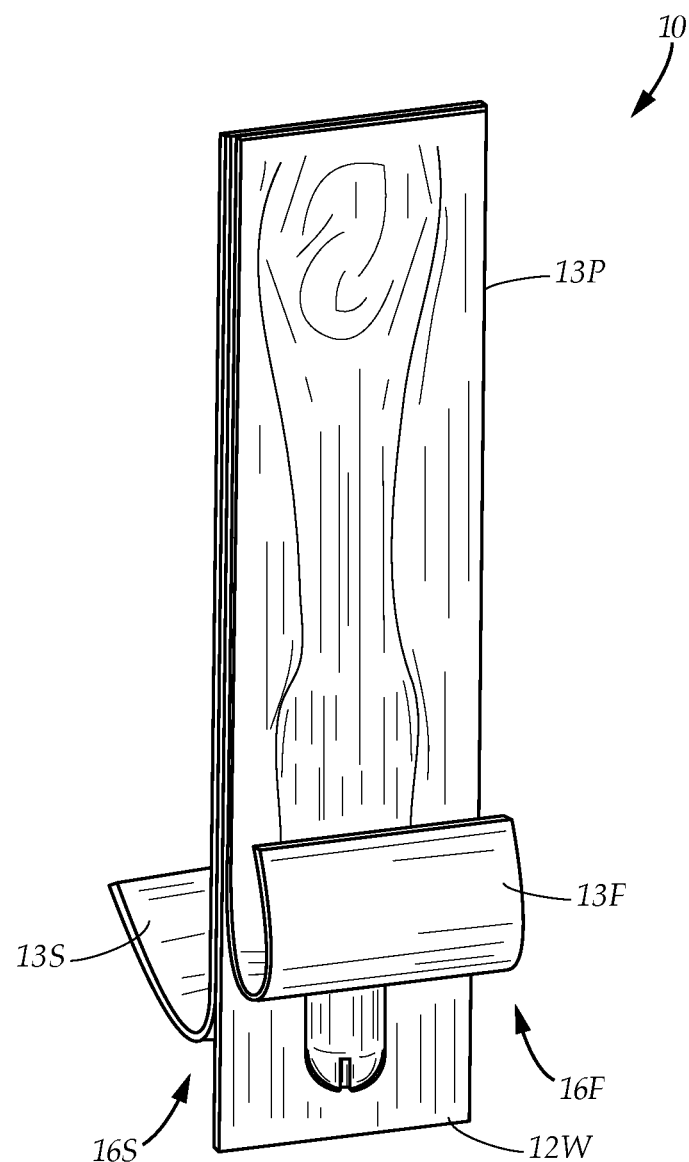
FIG. 1A is a perspective view of a first example embodiment of a feminine hygiene product disposal pouch having an outer wall defining an inner compartment and a partitioning wall defining a pair of inner chambers.
Figure 1B:
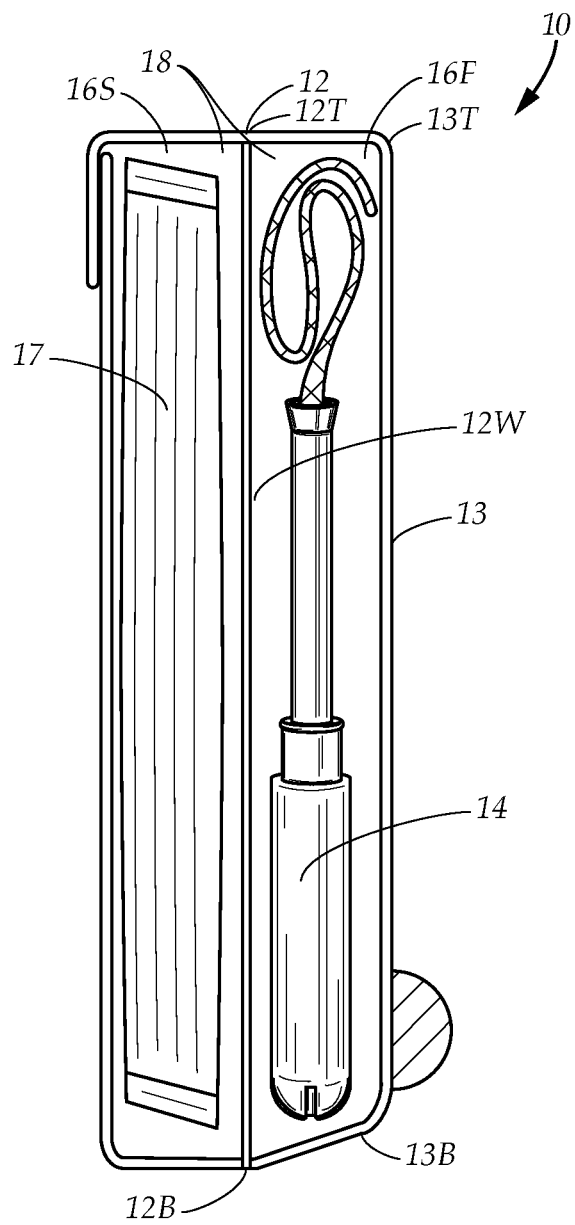
FIG. 1B is a side elevational view, with parts broken away, of the first example embodiment including a feminine hygiene product and a disposal container.
Figure 1C:
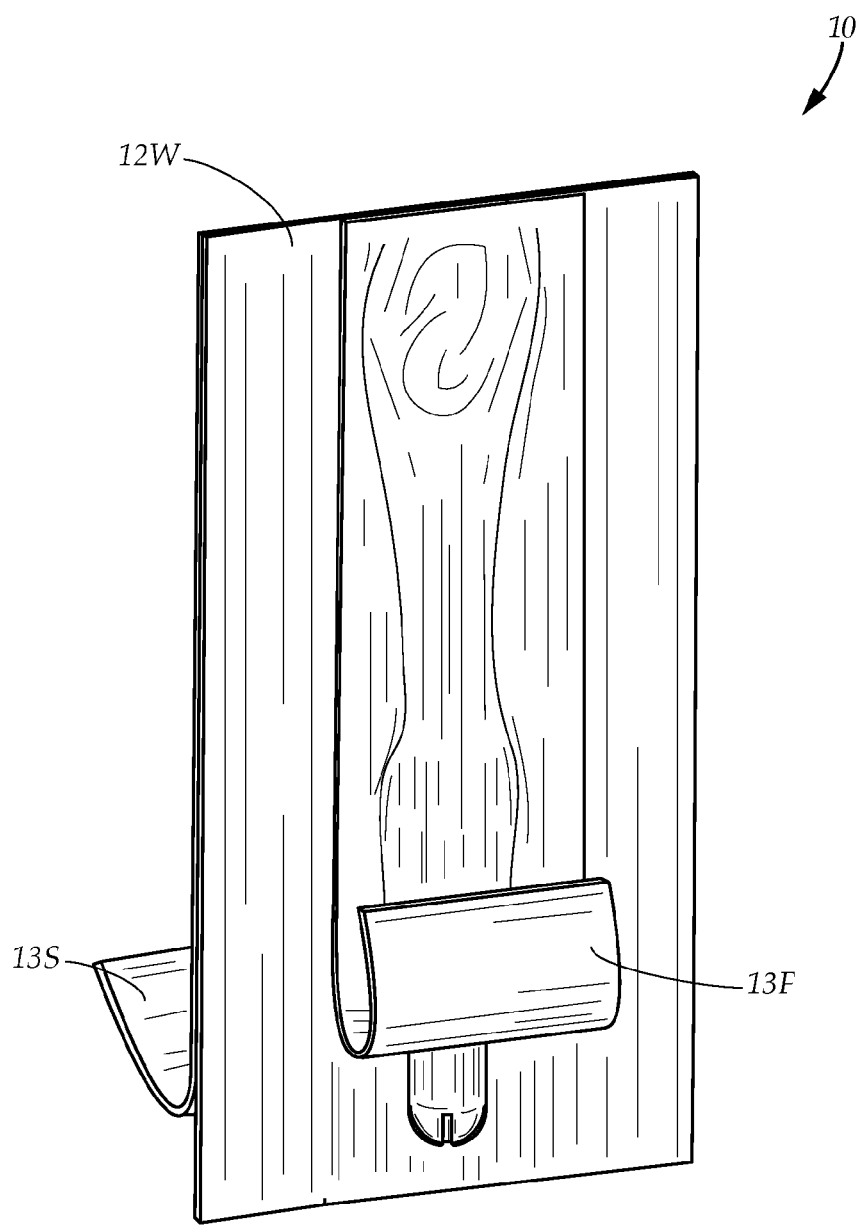
FIG. 1C is a perspective view of the first example embodiment wherein the pair of inner chambers are variably-sized.
Figure 4:
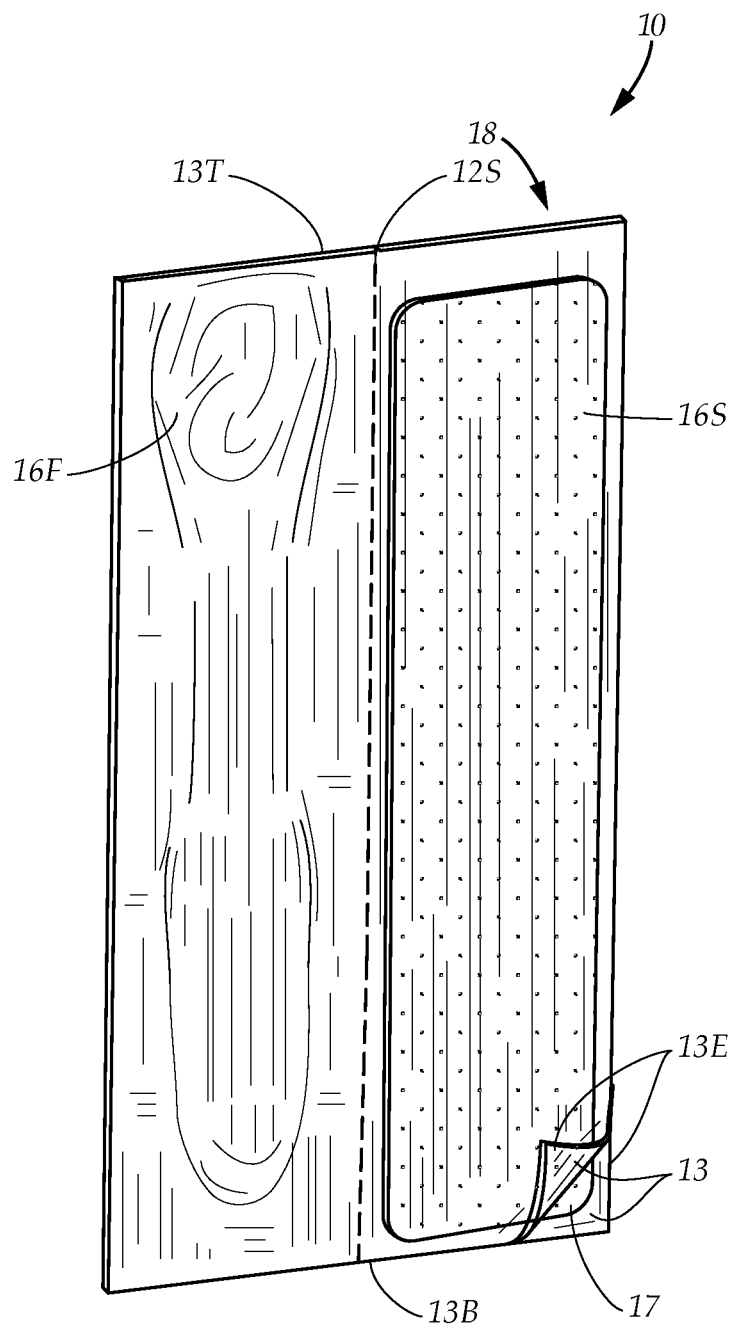
FIG. 4 is a perspective view of a second example embodiment of the feminine hygiene product disposal pouch having an outer wall and a partitioning seam defining a pair of inner chambers.

FIG. 1B illustrates a feminine hygiene product disposal pouch 10 providing a compact, hygienic solution for packaging and disposing of a plurality of feminine hygiene materials, such as a tampon 14, a tampon applicator, a disposal container 17, a feminine hygiene wipe, a baby wipe, and/or toilet paper. The pouch 10 includes an outer wall 13 having a top edge 13T and a bottom edge 13B. The outer wall 13 defines an inner compartment 18. The pouch 10 further includes at least one partitioning barrier 12 which traverses the inner compartment 18 to define a first inner chamber 16F and an opposing second inner chamber 16S with the outer wall 13. The partitioning barrier has a barrier top 12T which is substantially aligned with the top edge 13T of the outer wall 13 and a barrier bottom 12B which is substantially aligned with the bottom edge 13B of the outer wall. In the example embodiment illustrated in FIG. 1B, the partitioning barrier is a partitioning wall 12W which is operably coupled to the outer wall 13. In FIG. 4, however, the partitioning barrier is a partitioning seam 12S. The first inner chamber 16F is adapted to hold the feminine hygiene material 14. The second inner chamber 16S includes the disposal container 17 which will be described more in detail hereinbelow. It is understood that the shape of the pouch 10 can include, but is not limited to a circle, a triangle, a square, a cylinder, a cube, and a pyramid. Further, the partitioning barrier 12 can be directly coupled to the outer wall 13 using such means as, but not limited to, adhesives, glues, hook and eye fasteners, tape, and/or thermal bonding.

Figure 2:
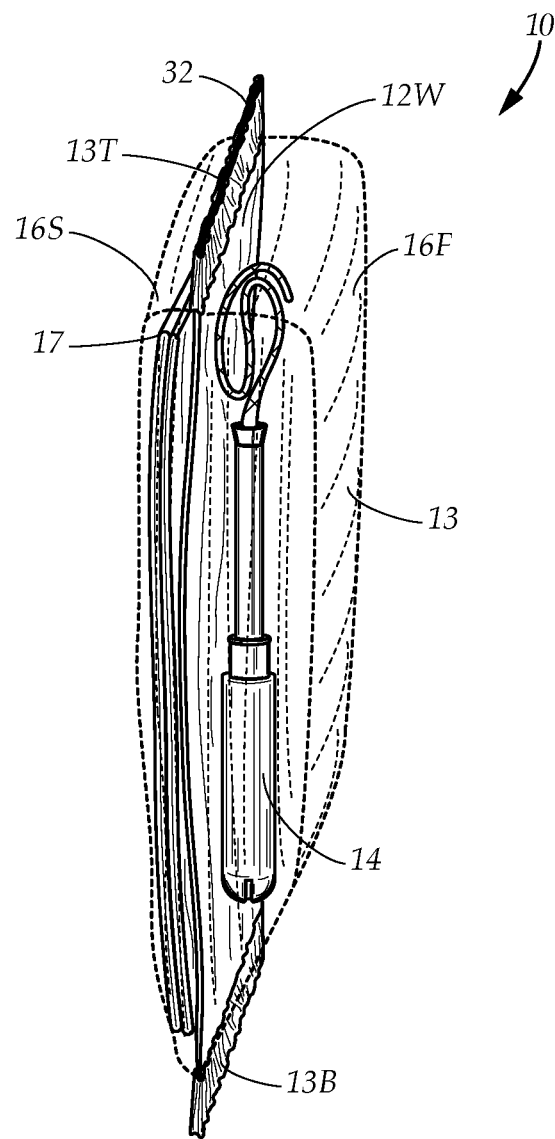
FIG. 2 is a perspective view of yet another example embodiment of the first example embodiment wherein the inner chambers share a common sealed edge.
Figure 3A:
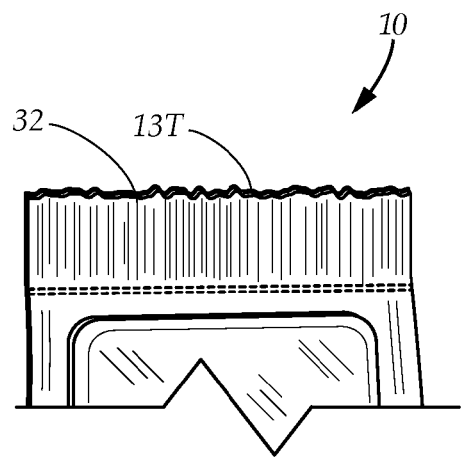
FIG. 3A, similar to FIG. 2, is a front elevational, enlarged view of the common sealed edge of the feminine hygiene product disposal pouch including an unbroken seal.
Figure 3B:
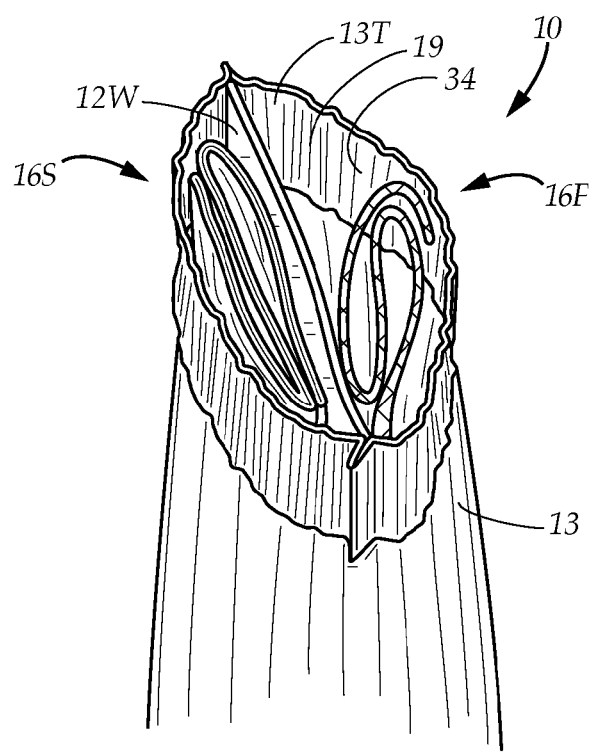
FIG. 3B is a perspective, enlarged view of the common sealed edge of the feminine hygiene product disposal pouch including a broken seal.

The outer wall 13 can extend continuously around the pouch 10, as illustrated in FIGS. 2, 3A and 3B. When thus configured, the pouch 10 can include a seal 32 formed between at least one of the top edge 13T and bottom edge 13B of the outer wall 13 directly, or between at least one of said edges 13T,13B and the partitioning wall 12W. The seal 32 can be a heat, crimped seal, such as that illustrated in FIG. 3A. The seal can include such features as a perforation to further assist a user in tearing the pouch. Further, to break the seal 32 as illustrated in FIG. 3B, the at least one of the top edge 13T or bottom edge 13B separate from each other or from the partitioning wall 12W, such as via an outward pulling force, to define an opening 19 which enables simultaneous access to both inner chambers 16F,16S.

Referring now to FIGS. 6A-6C, the pouch 10 can further be expandable to enable the hygienic disposal of a larger number of feminine hygiene materials. More particularly, at least one inner chamber 16 can include a pair of expandable side walls 52 oriented between the outer wall 13 and the partitioning wall 12W. The side walls 52 extend away from the partitioning wall 12W when in an expanded position, and can fold inwardly towards one another within the inner chamber 16 when in a collapsed position. FIG. 6B illustrates the side walls 52 which are pleated and/or fan folded to more efficiently enable their collapsibility. Further, FIG. 6C illustrates an inner chamber 16S including a closable covering 54, such as a flap, for selectively closing and sealing the compartment 16. The covering 54 has a first edge 54F which is coupled to at least one of the outer wall 13 and/or the partitioning wall, and a second edge 54S for coupling to a point elsewhere on the pouch 10 when resealing the compartment 16S.

Referring now to FIG. 4, the pouch 10 can further include the outer wall 13 having a pair of longitudinal edges 13E which are aligned and operably joined to define the inner compartment 18. The pouch 10 includes a partitioning seam 12S which traverses the inner compartment 18 between the top and bottom edges 13T, 13B. The partitioning seam 12S is oriented between and extends substantially parallel to the longitudinal edges 13E of the outer wall 13 thereby defining the opposing inner chambers 16F,16S. The longitudinal edges 13E can be separated from each other to enable access to each inner chamber 16F,16S in succession. Further, the outer wall 13 can be of uniform and/or varying materials and translucencies to enable the user to see at least one of the feminine hygiene materials through the pouch 10, such as the disposal container in FIG. 4.

In a further example embodiment of the pouch illustrated in FIG. 1A, the partitioning wall 12W full bisects the outer wall 13. When thus configured, the first inner chamber 16F is enclosed via a first outer wall 13F and the second inner 16S chamber is enclosed via a second outer wall 13S. Each outer wall 13F,13S includes a peripheral edge 13P to which the partitioning wall 12W is operably coupled. Further, in this example embodiment, a user is able to independently uncouple each outer wall 13F,13S from the partitioning wall 12W, such as via a pull-tab, without disturbing the opposing outer wall to enable selective access to the feminine hygiene material and disposal container housed, respectively, therein. The outer walls 13F, 13S and the partitioning wall 12W each have a lateral width which can be uniform and/or variable, as illustrated in FIG. 10, to produce inner chambers 16F,16S which are uniformly and/or variably sized. More particularly, as illustrated in FIG. 10, the second outer wall 13S and the partitioning wall 12W can have a lateral width which is substantially equal and greater than the lateral width of the first outer wall 13F to better accommodate the size of the disposal container enclosed therein. It is understood that in all the aforementioned pouch embodiments, each inner chamber 16F, 16S can include a coupling means, such as an adhesive, for operably resealing each chamber after the feminine hygiene materials have been removed and/or inserted therein.

Figure 5A:
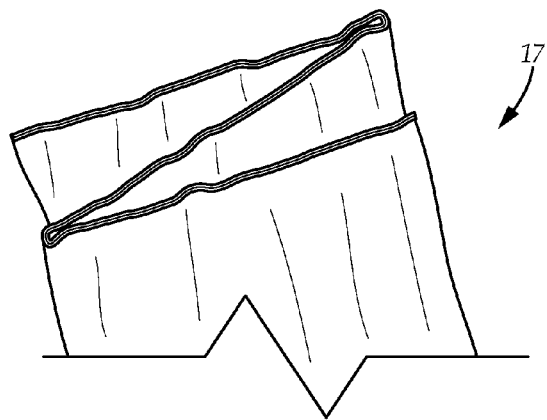
FIG. 5A is a perspective, enlarged view of an example embodiment of a Z-folded disposal container.
Figure 5B:
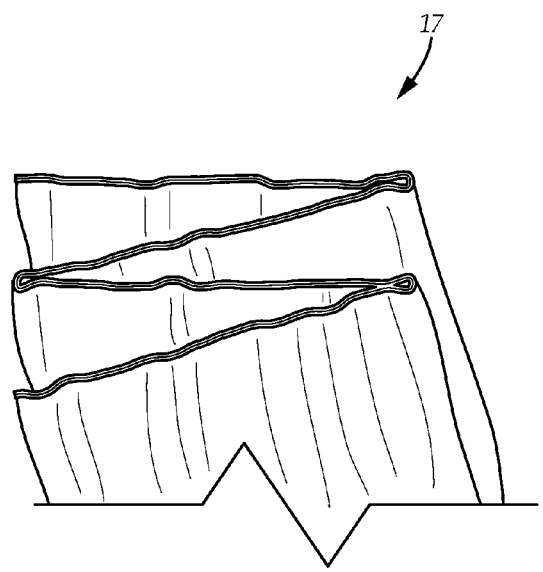
FIG. 5B is a perspective, enlarged view of an example embodiment of an accordion-folded disposal container.

FIG. 5A illustrates an example embodiment of the disposal container 17 described hereinabove, wherein it is a z-folded pouch. In another example embodiment shown in FIG. 5B, the disposal container 17 is an accordion-folded pouch. The disposal container 17 can be sealable such as via an adhesive or a cord and/or reusable. It is understood that the example embodiments of the disposal container described herein are non limiting and various other embodiments are anticipated by the present disclosure.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a feminine hygiene product disposal pouch. The disclosure is illustrated by example in the drawing figures, and throughout the written description. It should be understood that numerous variations are possible, while adhering to the inventive concept. Such variations are contemplated as being a part of the present disclosure.

What is claimed is:

1. A feminine hygiene product disposal pouch adapted for housing at least one feminine hygiene material and a disposal container, comprising:
   an outer wall having a top edge and a bottom edge, the outer wall defining an inner compartment;
   at least one partitioning barrier traversing the inner compartment, the partitioning barrier having a barrier top substantially aligned with the top edge of the outer wall and a barrier bottom substantially aligned with the bottom edge of the outer wall, the partitioning barrier and the outer wall together defining a first inner chamber adapted to hold a feminine hygiene material and a second inner chamber, the partitioning barrier is a partitioning wall which extends within the inner compartment between the top and bottom edge and is operably coupled to the outer wall;
   a disposal container housed within the second inner chamber;
   a seal formed between the at least one of the edges of the outer wall and the partitioning wall, such that the at least one of the top or bottom edges defines an opening which enables simultaneous access to both inner chambers when the seal is broken; and
   wherein the first and second inner chambers oppose one another thereby providing a compact solution for packaging and hygienically disposing of the disposal container and feminine hygiene material.

2. The feminine hygiene product disposal pouch as described in claim 1, wherein the seal is a heat seal.

3. The feminine hygiene product disposal pouch as described in claim 2, wherein at least one inner chamber includes a pair of expandable side walls oriented between the outer wall and the partitioning wall, the side walls extending away from the partitioning wall when in an expanded position, and folding inwardly towards one another within the inner chamber when in a collapsed position.

4. The feminine hygiene product disposal pouch as described in claim 3, wherein each of the first outer wall, the second outer wall, and the partitioning wall have a lateral width, the lateral width of the second outer wall and the partitioning wall which are substantially equal and greater than the lateral width of the first outer wall.

5. The feminine hygiene product disposal pouch as described in claim 1, wherein the disposal container is stored in the inner chamber in a folded configuration selected from the group consisting of a z-fold and an accordion fold.

6. A unitary feminine hygiene product disposal wrapper for independently housing at least one feminine hygiene material and at least one disposal container, comprising:
   a first inner chamber including a first chamber outer wall having a first chamber top and a first chamber bottom, the first inner chamber configured to hold the feminine hygiene material;
   a second inner chamber opposing the first inner chamber, the second inner chamber including a second chamber outer wall having a second chamber top substantially aligned with the first chamber top and a second chamber bottom substantially aligned with the first chamber bottom, the second inner chamber configured to hold the disposal container; and
   wherein the feminine hygiene product disposal wrapper further includes a partitioning barrier having a barrier top substantially aligned with the first and second chamber tops and a barrier bottom substantially aligned with the first and second chamber bottoms, the partitioning barrier operably coupled between the first and second chamber outer walls to fully enclose each chamber with the outer walls, and adapted to independently house the feminine hygiene material and disposal container therein, the first and second chamber tops include a seal formed between the tops and the partitioning wall, such that the first and second chamber tops define a feminine hygiene disposal wrapper opening which enables simultaneous access to both the first and second inner chamber when the seal is broken.

7. The feminine hygiene product disposal wrapper as described in claim 6, wherein the partitioning barrier is a partitioning wall.

8. The feminine hygiene product disposal wrapper as described in claim 6, wherein the seal is a heat seal.

9. The feminine hygiene product disposal wrapper as described in claim 7, wherein at least one of the first and second inner chamber includes a pair of expandable side walls oriented between the outer wall and the partitioning wall, the side walls extending away from the partitioning wall when in an expanded position, and folding inwardly towards one another within the inner chamber when in a collapsed position.

10. The feminine hygiene product disposal wrapper as described in claim 7, wherein each of the first and second outer wall has a perimeter edge to which the partitioning wall is operably coupled, and wherein each of the first and second outer wall can be independently uncoupled from the partitioning wall to enable selective access to the feminine hygiene material and disposal container housed, respectively, therein.

11. The feminine hygiene product disposal wrapper as described in claim 9, wherein each of the first outer wall, the second outer wall, and the partitioning wall have a lateral width, the lateral width of the second outer wall and the partitioning wall which are substantially equal and greater than the lateral width of the first outer wall.

12. The feminine hygiene product disposal pouch as described in claim 1, wherein the partitioning wall fully bisects the outer wall such that the first inner chamber is enclosed via a first outer wall and the second inner chamber is enclosed via a second outer wall, each outer wall having a perimeter edge to which the partitioning wall is operably coupled, and wherein each of the first and second outer wall can be independently uncoupled from the partitioning wall to enable selective access to the feminine hygiene material and disposal container housed, respectively, therein.

* * * * *